United States Patent [19]

Gallagher et al.

[11] Patent Number: 4,983,619
[45] Date of Patent: Jan. 8, 1991

[54] PHARMACEUTICAL COMPOUNDS

[75] Inventors: Peter T. Gallagher, Yateley; Terence A. Hicks, Fleet, both of England

[73] Assignee: Lilly Industries Limited, Basingstoke, England

[21] Appl. No.: 464,644

[22] Filed: Jan. 11, 1990

Related U.S. Application Data

[63] Continuation of Ser. No. 372,148, Jun. 26, 1989, abandoned, which is a continuation of Ser. No. 83,531, Aug. 7, 1987, abandoned.

[30] Foreign Application Priority Data

Aug. 8, 1986 [GB] United Kingdom ............... 8619433

[51] Int. Cl.$^5$ .................. A61K 31/425; A61K 31/40; C07D 333/36; C07D 307/02
[52] U.S. Cl. ........................ 514/371; 514/372; 514/426; 514/447; 514/472; 549/69; 549/480; 548/195; 548/206; 548/557; 548/558
[58] Field of Search ............... 549/69, 480; 548/375, 548/233, 337, 557, 558, 309, 206; 544/323, 329; 514/447, 472, 426, 371, 372

[56] References Cited

U.S. PATENT DOCUMENTS 4,061,767 12/1977 Ertel et al. .................. 424/282

FOREIGN PATENT DOCUMENTS

| 21207 | 1/1981 | European Pat. Off. . |
| 2655009 | 6/1978 | Fed. Rep. of Germany . |
| 1571990 | 7/1980 | United Kingdom . |
| 1596383 | 8/1981 | United Kingdom . |
| 1598900 | 9/1981 | United Kingdom ........ 548/375 |

Primary Examiner—Alan Siegel
Attorney, Agent, or Firm—Robert A. Conrad; Leroy Whitaker

[57] ABSTRACT

Compounds of the following formula have pharmaceutical properties:

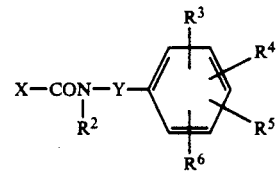

in which X is $R'(HO)C=C(CN)-$, $R^1(CO)-CH(CN)-$ or

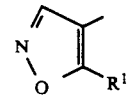

$R^1$ and $R^2$ are each hydrogen or $C_{1-6}$ alkyl, $R^3$, $R^4$, $R^5$ and $R^6$ are each hydrogen, hydroxy, halogen, nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio, $C_{2-5}$ alkoxycarbonyl, optionally substituted phenyl, optionally substituted phenoxy, R'R"N— where R' and R" are each hydrogen or $C_{1-4}$ alkyl or R'''CONH— where R''' is $C_{1-4}$ alkyl, or a group of the formula $-CR^7R^8R^9$ in which $R^7$, $R^8$ and $R^9$ are each $C_{1-6}$ alkyl, halo-substituted $C_{1-6}$ alkyl or optionally substituted phenyl, or $R^7$ and $R^8$, together with the carbon atom to which they are attached, form a cycloalkyl group containing 3 to 7 carbon atoms, or $R^7$, $R^8$ and $R^9$ together with the carbon atom to which they are attached, form a bicycloalkyl group containing 4 to 9 carbon atoms, and Y is a 5- or 6-membered heterocyclic ring excluding pyrazole; and salts thereof.

8 Claims, No Drawings

PHARMACEUTICAL COMPOUNDS

This application is a continuation of application Ser. No. 7/372,148, filed June 26, 1989, now abandoned, which is a continuation of application Ser. No. 07/083,531, filed as Aug. 7, 1987, now abandoned.

This invention relates to novel compounds and their use as pharmaceuticals.

Certain phenyl butenamide compounds with pharmaceutical properties are disclosed in British Pat. No. 1 571 990. The compounds are optionally substituted with various substituents on the phenyl nucleus including methyl or ethyl.

By contrast the compounds of the invention are substituted heterocyclic derivatives. They have the following general formula

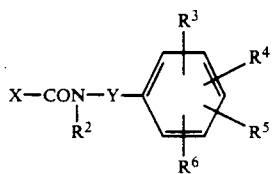
(I)

in which X is $R^1(HO)C=C(CN)-$, $R^1(CO)-CH(CN)-$ or

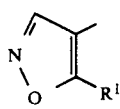

$R^1$ and $R^2$ are each hydrogen or $C_{1-6}$ alkyl, $R^3$, $R^5$ and $R^6$ are each hydrogen, hydroxy, halogen, nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio, $C_{2-5}$ alkoxycarbonyl, optionally substituted phenyl, optionally substituted phenoxy, $R'R''N$—where $R'$ and $R''$ are each hydrogen or $C_{1-4}$ alkyl or $R'''CONH$—where $R'''$ is $C_{1-4}$ alkyl, or a group of the formula $-CR^7R^8R^9$ in which $R^7$, $R^8$ and $R^9$ are each $C_{1-6}$ alkyl, halo-substituted $C_{1-6}$ alkyl or optionally substituted phenyl, or $R^7$ and $R^8$, together with the carbon atom to which they are attached, form a cycloalkyl group containing 3 to 7 carbon atoms, or $R^7$, $R^8$ and $R^9$ together with the carbon atom to which they are attached, form a bicycloalkyl group containing 4 to 9 carbon atoms, and Y is a 5- or 6-membered heterocyclic ring excluding pyrazole; and salts thereof.

The compounds of the invention and their pharmaceutically-acceptable salts are active in tests which show their potential for treating immune diseases such as arthritis, and for treating diseases in which leukotrienes are implicated.

It will be appreciated that compounds of the formula (I) above, in which X is $R^1(HO)C=C(CN)-$, can exist in tautomeric and isomeric form as indicated by the following equilibria:

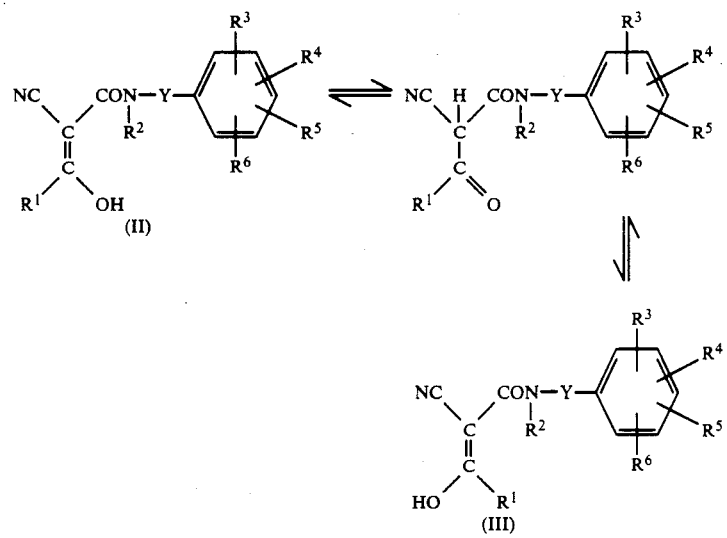

When prepared by the usual methods of synthesis the compounds are a mixture of the Z and E isomers, (II) and (III) above, in which the Z form predominates. The Z and E forms can be separated by conventional crystallisation techniques. The keto form is an intermediate in the synthesis of the isomers (11) and (111).

In formula (I) a $C_{1-6}$ alkyl group can be branched or unbranched and can be, for example, methyl, ethyl, propyl, 1-methylethyl, butyl, 1-methylpropyl, 1,1-dimethylethyl, pentyl or hexyl. Similarly a $C_{1-4}$ alkyl can be methyl, ethyl, propyl or 1-methylethyl, and $C_{1-4}$ alkoxy and $C_{1-4}$ alkylthio are derived from such groups being attached to the phenyl ring by an oxygen or sulphur atom, respectively. When such groups are halo-substituted one or more of the hydrogen atoms is replaced by a halo atom, which is preferably fluoro, chloro or bromo and especially fluoro or chloro. A preferred example of halo-substituted alkyl is the trifluoromethyl substituent. $R^3$, $R^4$, $R^5$ and $R^6$ can also be halogen and when halogen is preferably fluoro, chloro or bromo. When $R^3$, $R^4$, $R^5$ or $R^6$ is a $C_{2-5}$ alkoxycarbonyl group it is of the formula ROCO—where R is a $C_{1-4}$ alkyl group, and when $R^3$, $R^4$, $R^5$ or $R^6$ is optionally substituted phenyl or optionally substituted phenoxy, it is preferred that the phenyl group is optionally substituted with 1 to 3 groups selected from, halogen, nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio and $C_{2-5}$ alkoxycarbonyl.

When $R^7$ and $R^8$ form a cycloalkyl group, the cycloalkyl group can be cyclopropyl, cyclobutyl, cyclopentyl, cyclohexyl or cycloheptyl, and when $R^7$, $R^8$ and $R^9$ together form a bicyclo radical the radical preferably contains 4 to 7 carbon atoms, an example being bicyclo [4.1.0]heptyl.

The heterocyclic radical Y can be any 5- or 6-membered heterocyclic ring, with the exception of pyrazole, and examples include the radicals derived from thiophene, furan, pyrrole, pyridine, thiazole, isothiazole, oxazole, isoxazole, imidazole and pyrimidine. The point of attachment of the phenyl group and the α-cyano β-ketoamido group can be at any of the available carbon atoms on the heterocyclic ring. Preferred values of Y are the following disubstituted radicals:

2,5-thiophene,
2,4-thiophene,
2,5-furan,
2,5-pyrrole,
2,6-pyridine,
2,5-thiazole,
2,5-oxazole,
2,5-imidazole,
3,5-isothiazole, and
2,6-pyrimidine.

The heterocyclic radical may be substituted, if desired, by for example one or more, such as one or two, $C_{1-4}$ alkyl groups, especially methyl. In particular the nitrogen atom of the pyrrole nucleus can be alkylated.

It is, of course, possible to prepare salts of the compounds of the invention because of the presence of the acidic hydroxyl group. Such salts are included in the invention. They can be any of the well known base addition salts. Examples of such salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, calcium hydroxide, methylamine, diethylamine, ethylene diamine, cyclohexylamine and ethanolamine. The potassium and sodium salt forms are particularly preferred. There may in addition be other salt-forming groups on the phenyl ring, providing both base and acid addition salts. It is preferred that the salt is pharmaceutically-acceptable but other salts are included in the invention since they may be used in the preparation of other compounds or to obtain good crystalline forms.

Preferred compounds of formula (I) are those in which:

(i) X is $R^1(HO)C=C(CN)$—and more specifically

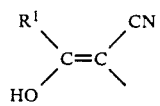

(ii) $R^3$, $R^4$ and $R^5$ are hydrogen
(iii) $R^2$ is hydrogen
(iv) $R^2$ is methyl
(v) $R^1$ is $C_{1-6}$ alkyl, preferably methyl
(vi) $R^6$ is hydrogen, $C_{1-4}$ alkyl, halo-substituted $C_{1-4}$ alkyl or —$CR^7R^8R^9$ in which $R^7$, $R^8$ and $R^9$ are each $C_{1-4}$ alkyl (vii) $R^6$ is —$CR^7R^8R^9$ and $R^7$, $R^8$ and $R^9$ are each $C_{1-4}$ alkyl
(viii) $R^7$ and $R^8$ together form a cycloalkyl group of 3 to 7 carbon atoms and $R^9$ is $C_{1-6}$ alkyl or phenyl.
(ix) the —$CR^7R^8R^9$ group is attached to the phenyl ring at the para position, with respect to the amido group A preferred group of compounds is of the formula

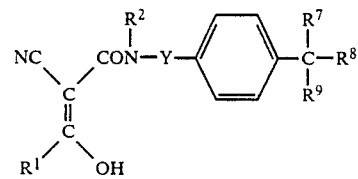

in which $R^1$ is $C_{1-4}$ alkyl, $R^2$ is hydrogen or methyl, and $R^7$, $R^8$ and $R^9$ are each hydrogen or $C_{1-4}$ alkyl; and salts thereof; and Y is preferably thiophene.

A further preferred group of compounds is of the formula

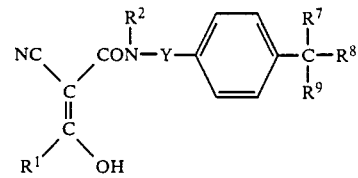

in which $R^1$ is $C_{1-4}$ alkyl, $R^2$ is hydrogen or methyl, $R^7$ and $R^8$ together form a cycloalkyl group of 3 to 7 carbon atoms and $R^9$ is $C_{1-4}$ alkyl or phenyl; and salts thereof; and Y is preferably thiophene.

The invention also comprises a process for producing compounds of formula (1) which comprises (a) reacting a compound of the formula

in which M is a monobasic metal ion, with a compound of the formula

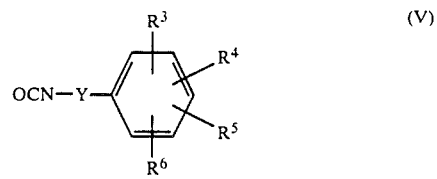

where $R^1$ and $R^3$ to $R^8$ have the values given above, and optionally reacting the salt thus formed with acid to liberate the free hydroxyl compound in which X is $R^1(HO)C=C(CN)$—, (b) reacting a compound of the formula

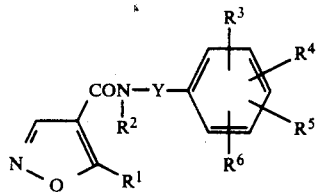

where $R^1$ to $R^8$ have the values given above, with base, and optionally reacting the salt thus formed with acid to liberate the free hydroxyl compound in which X is $R^1(HO)C=C(CN)—$, (c) reacting a compound of the formula

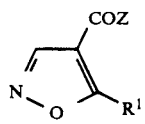

with an amine of the formula

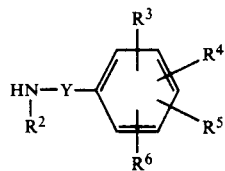

where Z is halo, preferably choro, to give a compound in which X is

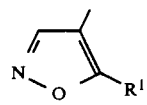

or
(d) hydrolysing a compound of the formula

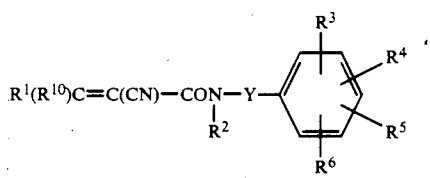

where $R^1$ to $R^6$ have the values given above and $R^{10}$ is a leaving group.

The reaction (a) referred to above is preferably carried out in an inert organic solvent such as for example tetrahydrofuran and at a temperature of from $-30°$ C. to $100°$ C., yielding a salt of the formula

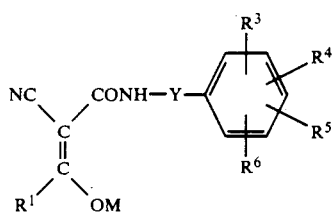

which can be converted to the free hydroxyl compound shown in formula (1) by action of acid such as aqueous mineral acid, for example hydrochloric acid, at a temperature of from $0°$ C. to $100°$ C. It is the preferred route for compounds of formula (I) in which Y is thiophene or furan.

Compounds of formula (IV) can be prepared by ring opening the appropriate isoxazole derivative of formula

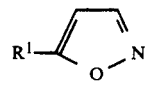

by the action of base such as, for example, alkali metal alkoxide in ethanol at a temperature of for example $5°$ C. to $80°$ C. to give a compound in which M is an alkali metal ion, or by reacting 5-methylisoxazole with butyl lithium in tetrahydrofuran at a temperature of from $-80°$ C. to $30°$ C. to give a compound in which M is lithium, optionally followed by reaction with the appropriate alkyl bromide or iodide to give reactants of formula (IV) in which $R^1$ is $C_{2-6}$ alkyl. Compounds of formula (V) can be synthesized by conventional methods such as by reacting the appropriate carboxylic acid derivative with diphenyl phosphoryl azide and triethylamine in dimethylformamide and heating the azide thus produced under reflux.

With regard to reaction (b), this reaction is preferably performed in an inert organic solvent such as for example tetrahydrofuran, ethanol or dimethylsulphoxide, at a temperature of from $-80°$ C. to $100°$ C.

Reactants of formula (VI) can be readily prepared by condensing an isoxazolyl halide of the formula

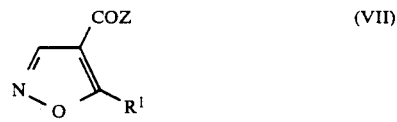

where Z is halo preferably chloro, with an appropriate amine of the formula

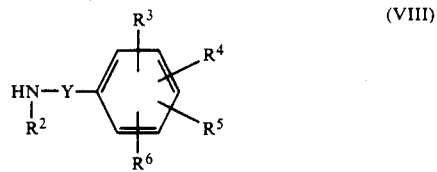

The reaction is preferably carried out at a temperature of from $-70°$ C. to $110°$ C. in an inert organic solvent such as for example toluene. Compounds of formula (VII) can be prepared by a sequence of reactions, for example, as follows

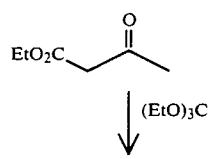

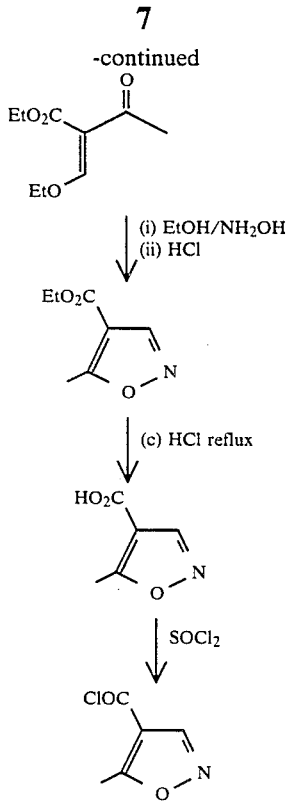

Compounds of formula (VIII) can be prepared by conventional methods, and for example in the case of compounds of formula (I) in which Y is oxazole by the method disclosed in J. Org. Chem. 1981, 46, 2069, van Leusen et al.

Those compounds of formula (VIII) in which $R^2$ is $C_{1-6}$ alkyl can be prepared from the corresponding amine by a suitable technique of alkylation, for example, by treatment with formyl acetic anhydride followed by reduction with lithium aluminium hydride to give the compound in which $R^2$ is methyl, or by acylation with the appropriate alkanoyl halide followed by reduction with lithium aluminium hydride to give compounds in which $R^2$ is $C_{2-6}$ alkyl. Alternatively the compounds can be prepared by reducing the corresponding isocyanate employing, for example, lithium aluminium hydride in ether.

The reaction (d), referred to above, is preferably carried out in aqueous medium at a temperature of from 5° C. to 100° C. Mineral acid such as hydrochloric acid or alkali metal base for example sodium hydroxide can be employed. $R^{10}$ is a leaving group that is removed in the hydrolysis reaction and is especially $C_{1-4}$ alkoxy, phenoxy or R'R"N—where R' and R" are each $C_{1-4}$ alkyl.

Compounds of formula (IX) can be prepared from the appropriate amine of formula

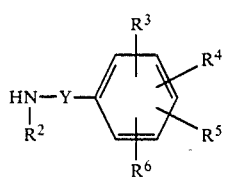

by reaction firstly with cyanoacetic acid or an ester of cyanoacetic acid, a reaction which proceeds by use of a dehydrating agent for example dicyclohexyl carbodiimide in a suitable solvent such as dichloromethane, or by the application of heat, to give a compound of formula

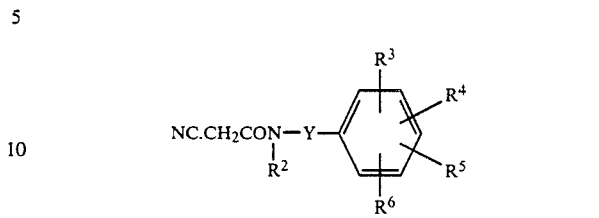

which on reaction with trialkylorthoacetate or higher alkanoate, in acetic anhydride and preferably with a catalytic amount of a Lewis acid such as zinc chloride, gives the desired intermediate.

It will be appreciated that the substituents on the phenyl ring shown in formula (I) can be interchanged. For instance a carboxyl substituent on the ring or a carboxyl attached to a phenyl substituent on the ring can be prepared by hydrolysis of the appropriate nitrile or alkoxycarbonyl derivative, after the main condensation reaction step has been performed.

The compounds of the invention have been shown to modify the immune response in tests which establish that they inhibit concanavalin A-induced T-cell proliferation and graft versus host reaction, a T-cell mediated process. The compounds are also active in the adjuvant arthritis test (B. B. Newbould Chemotherapy of Arthritis Induced in Rats by Mycobacterial Adjuvant, Br.J.Pharmacol. 21, 127–136 (1963)).

The above properties show that the compounds of the invention have anti-inflammatory properties and are indicated for used in the treatment of, for example, arthritis and also immune diseases such as systemic lupus and graft rejection.

Compounds of the invention also inhibit 5-lipoxygenase product formation as shown in the test described by J. Harvey and D. J. Osborne, J.Pharmacological Methods 9, 147–155 (1983), and are thus indicated for the therapeutic treatment of diseases in which leukotrienes are implicated. These include immediate hypersensitivity diseases, allergic reactions of the pulmonary system, for example, in lung disorders such as extrinsic asthma and industrial asthmas and in other inflammatory disorders associated with acute or chronic infectious diseases such as allergic skin diseases, ectopic and atopic eczemas, psoriasis, contact hypersensitivity and angioneurotic oedema, bronchitis, cystic fibrosis and rheumatic fever. Furthermore, owing to their inhibition of leukotriene formation, the compounds have potential activity against a wide range of inflammatory diseases, and are also indicated for use in cancer treatment.

The compounds may be administered by various routes, for example, by the oral or rectal route, by inhalation, topically or parenterally, for example by injection, being usually employed in the form of a pharmaceutical composition. Such compositions form part of the present invention and are prepared in a manner well known in the pharmaceutical art and normally comprise at least one active compound in association with a pharmaceutically acceptable diluent or carrier. In making the compositions of the present invention, the active ingredient will usually be mixed with a carrier, or diluted by a carrier, and/or enclosed with a carrier which may, for example, be in the form of a capsule, sachet, paper or other container. There the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, aerosols, as a solid or in a liquid medium, ointments containing, for example, up to 10% by weight of the active compound, soft and hard gelatin capsules, suppositories, injection solutions and suspensions and sterile packaged powders. For administration by inhalation, particular forms of presentation include aerosols, atomisers and vaporisers.

Some examples of suitable carriers are lactose, dextrose, sucrose, sorbitol, mannitol, starch, gum acacia, calcium phosphate, alginates, tragacanth, gelatin, syrup, methyl cellulose, methyl-and propyl- hydroxybenzoate, talc, magnesium stearate and mineral oil. The compositions of the invention may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, more usually 25 to 200 mg, of the active ingredient. The term "unit dosage form" refers to physically discrete units suitable as unit dosage for human subjects and animals, each unit containing a predetermined quantity of active material calculated to produce the desired therapeutic effect, in association with the required pharmaceutical carrier.

The compounds are effective over a wide dosage range and for example dosages per day will normally fall within the range of 0.5 to 300 mg/kg and in the treatment of adult humans, more usually in the range of from 5 to 100 mg/kg. However, it will be understood that the amount of the compound actually administered will be determined by a physician, in the light of the relevant circumstances including the condition to be treated, the choice of compound to be administered and the chosen route of administration and therefore the above dosage ranges are not intended to limit the scope of the invention in any way.

The following Examples illustrate the invention. The compounds of formula (I) in which X is $R^1(HO)C=C(CN)$— are prepared initially as a mixture of Z and E isomers in which the Z form predominates. On purification the pure Z isomer was obtained as the product.

EXAMPLE 1

(i) Cyanoacetone, Sodium Salt

Sodium lumps (7.36 g) were allowed to dissolve, with mechanical stirring, in absolute ethanol (368 ml), the reaction being carried out under nitrogen. The resulting hot solution was stirred until temperature fell to about 20° C.

5-Methylisoxazole (26.56 g) was added dropwise during 12 minutes. The resulting hot white suspension was stirred for 1 hour 12 minutes, then cooled in an ice-bath and stirred for 1 hour 24 minutes.

The white solid was removed by filtration, and washed on the filter with 40°-60° C. petroleum ether (50 ml). It was dried in vacuo in the oven at 46° C., to give cyanoacetone, sodium salt.

(ii) 2-(4-Trifluoromethylphenyl)thiophene

4-Aminobenzotrifluoride (25 g) was added to water (62.5 ml) and concentrated hydrochloric acid (35 ml) with vigorous mechanical stirring in a flask, to produce a thick white suspension.

The suspension was cooled in a $EtOH/CO_2$ bath, and a solution of sodium nitrite (11.3 g) in water (39 ml) added from a dropping funnel at 0°-3° C. over 15 minutes.

The resulting thin cream coloured suspension was stirred for 24 minutes at 1° C. to 3° C., then thiophene (128.6 ml; 136.35 g) was added during 3 minutes at 1° C. to 3° C., followed by the addition, one minute later, of a solution of sodium acetate (anhydrous) (62.33 g), in water (156 ml) over 4 minutes at 1.5° C.-3° C.

The reaction mixture was stirred mechanically for 3.5 hours at 0° C.-5° C., then magnetically at room temperature for 62.5 hours.

The reaction mixture was transferred to a separating funnel. The lower aqueous layer was removed and extracted with ether (2×75 ml).

The ether extracts were combined with an upper dark brown organic layer, washed with water (4×15 ml), dried over $MgSO_4$ filtered and evaporated from the steam bath at the water pump, to leave a gummy brown solid.

The solid was dissolved in boiling absolute ethanol (40 ml) and was left cooling in an ice-bath for 46 minutes, then filtered. The brown solid on the filter was washed with ice-cold absolute ethanol (3 x 10 ml). The resulting cream coloured solid was dried overnight in a vacuum desiccator over silica gel, 2-(4"-trifluoromethylphenyl)thiophene, m.p. 114.5° C.

(iii) 5-(4-Trifluoromethylphenyl)thiophen-2-carboxylic acid 2-(4-Trifluoromethylphenyl)thiophene (20.387 g) was magnetically stirred in 3A molecular sieve-dried ether (267 ml) under nitrogen and in apparatus that had been oven dried.

The solution was cooled in an ice-bath and 1.6 M butyl lithium in hexane (78.6 ml) added during 22 minutes at 4° C.-8° C.

The mixture was stirred for a further 44 minutes in an ice-bath, then cautiously added to a slurry of powdered $CO_2$ in ether (to make a total volume of slurry of about 267 ml), with hand stirring over approximately 2 minutes.

The mixture was kept for 9 minutes, with occasional stirring, then water (400 ml) was very cautiously added during 3 minutes with hand stirring. It was then transferred to a separating funnel. The ether layer was removed and washed with water (1×100 ml) and the main aqueous layer was washed with ether (1×100 ml).

The combined aqueous phases were adjusted to pH 1 by addition of concentrated HCl and a cream coloured solid precipitated. This was filtered off and washed on the filter with water (total volume 1 liter). The final washing had pH 5.

The product was dried in a vacuum desiccator over silica gel, to give 5-(4-trifluoromethylphenyl)thiophen-2-carboxylic acid, m.p. 227° C.

(iv) 2-Azidocarbonyl-5-(4-trifluromethylphenyl)thiophene

The acid (21.241 g) was magnetically stirred in 4A molecular sieve-dried dimethylformamide (74 ml), under nitrogen, and in apparatus that had been oven dried.

Triethylamine (14.5 ml; 10.6 g) was added and stirring continued at ambient temperature until complete dissolution had occurred.

The mixture was cooled in an EtOH/CO₂ bath and a solution of diphenylphosphoryl azide (21.47 g) in dry dimethylformamide (10 ml) added during 26 minutes at 0° C.-2° C.

The cooling bath was replaced by an oil-bath. The brown solution was heated at 35° C.±2° C. for 1.5 hours, and then left to cool at ambient temperature for 66.5 hours.

The brown solution was poured on to ice (about 500 ml) and a cream coloured solid precipitated. This was extracted into ethyl acetate (1×250 ml; 2×100 ml) and the combined extracts were washed with saturated aqueous sodium bicarbonate (4×25 ml), then water (4×25 ml). The extracts were dried over MgSO₄, filtered and evaporated in vacuo at 43° C. to leave a beige-coloured solid, 2-azidocarbonyl-5-(4-trifluoromethylphenyl)thiophene, m.p. 97° C.

(v) 2-Isocyanato-5- (4-trifluoromethylphenyl)thiophene

The azide (22.179 g) was magnetically stirred in 4A molecular sieve dried toluene (400 ml), under nitrogen, then brought to reflux in a mantle to give a clear solution.

The reaction mixture was stirred at reflux for 1 hour 12 minutes. The resulting brown turbid solution was stirred in an ice-bath for 3 hours, then filtered to remove a cream coloured solid, which was washed on the filter with toluene (50 ml), then 40°-60° C. petroleum (20 ml) and dried over silica gel in a vacuum desiccation.

The filtrate and washings were combined and evaporated in vacuo at 73° C. to leave a light brown oil, which solidified on cooling to room temperature. This was stirred in 40°-60° C. petroleum (100 ml), filtered and washed on the filter with 40°-60° C. petroleum (2×20 ml). The solid was dried in a vacuum desiccator over silica gel, 2-isocyanato-5-(4-trifluoromethylpenyl)-thiophene, m.p. 64° C.

(vi)
2-Cyano-3-hydroxy-N-[5-(4-trifluoromethylphenyl)-thien-2-yl]but-2-enamide

Cyanoacetaone, sodium salt (6.41 g), was magnetically stirred in freshly sodium dried and distilled tetrahydrofuran (105 ml) under nitrogen and in oven dried apparatus. The solution was cooled in an ice-bath and a turbid solution of ground isocyanate (16.45 g) in dry tetrahydrofuran (66 ml) added during 15 minutes at 1° C.-4° C.

The cooling bath was removed and the brown suspension was allowed to stir for 9 minutes before heating to 50° C. in an oil-bath, then stirred at 52° C.-53° C. for 2 hours 13 minutes. The mixture was kept under nitrogen for 67 hours at room temperature. It was filtered to remove a cream coloured solid and washed on the filter with a little tetrahydrofuran, then dried at 46° C. under vacuum in an oven.

The filtrate and washings were combined and evaporated in vacuo to leave a brown solid foam. This was stirred in water (550 ml) and brought to pH 12 by addition of 2N NaOH (25 ml) and washed with ether.

The aqueous phase was filtered to remove a little insoluble solid, then adjusted to pH 1 by addition of concentrated HCl, with stirring.

The cream coloured solid which precipitated was filtered off and washed on the filter with water (750 ml), dried at 46° C. in a vacuum oven.

The product was dissolved in boiling ethyl acetate (300 ml), filtered hot to clarify and left to stand at ambient temperature for 19 hours.

A cream coloured crystalline solid was filtered off and dried at 46° C. in a vacuum oven, 2-cyano-3-hydroxy-N-[5-(4-trifluoromethylphenyl)thien-2-yl]but-2-enamide, m.p. 245°-246° C.

EXAMPLE 2

(i) 2-[4-(1,1-Dimethylethyl)phenyl]thiophene

1-Bromo-4-(1,1-dimethyl)ethylbenzene (100 g) in dry and distilled tetrahydrofuran (150 ml) was added in portions to a magnetically stirred suspension of magnesium metal (11.67 g) in dry and distilled tetrahydrofuran (100 ml). After initiation of the Grignard reaction by heating, the 1-bromo-4-(1,1-dimethylethyl)benzene was added at such a rate that the solvent boiled. After the addition the reaction mixture was heated under reflux for two hours. The reaction mixture was cooled to room temperature and poured cautiously into an ice-cooled solution of 2-bromothiophene (76.51 g) in dry and distilled tetrahydrofuran (250 ml) containing dichloro-bis-(1,3-diphenylphosphino) propane nickel II (0.15 g) (see G. R. VanHecke and W. D. Horrocks, Inorg. Chem., 1966, 5 1968). After the solution of 4-(1,1-dimethylethyl)phenyl magnesium bromide had been added, the ice bath was removed and then in 0.1-0.2 g portions more dichlorobis-(1,3-diphenylphosphino)propane nickel II (2.75 g) was added over 0.75 hours using the ice bath where necessary to bring the reaction mixture back to room temperature. After all the catalyst had been added the black-brown solution was stirred and heated under reflux for 2 hours and then allowed to stand for 16 hours. The precipitated magnesium bromide was separated by decantation and washed with tetrahydrofuran and separated by decantation. The magnesium bromide was then dissolved in water (500 ml) extracted with ethyl acetate (2×200 ml). This was combined with the decanted solution and diluted to 1500 ml with ethyl acetate. This was washed with sodium hydrogen carbonate solution, dried (MgSO₄), charcoaled and filtered (3x) and the solvent removed in vacuo to give a brown oil (86.57 g). This oil was distilled using a Claisen still-head at 80°-120° C./0.65 mm Hg., then redistilled through a 20 cm×2 cm Vigreux column jacketed with cotton wool and using an air condenser. The fraction b.p. 100°-112° C./0.35 mm Hg was collected to give 2-(4-(1,1-dimethylethyl)phenyl)-thiophene.

(ii)
2-Carboxy-5-[4-(1,1-dimethylethyl)phenyl]thiophene

2-[4-(1,1-Dimethylethyl)phenyl]thiophene (111.6 g) was dissolved in 3A molecular sieve dried ether (1145 ml), with mechanical stirring.

The solution was cooled to 0° C. by means of an ethanol/CO₂ bath, then 1.55 M n-butyl lithium in hexane (458 ml) was added dropwise during 46 minutes at 0 to 19° C.

Stirring was continued for a further 2 hours, allowing the temperature gradually to rise from −19° to 0° C. during this period.

The reaction mixture was then transferred, by means of nitrogen pressure and via a glass tube, into a mechanically stirred slurry of carbon dioxide pellets (approximately 1730 g of pellet size 2×1 cm) in ether (575 ml), during 15 minutes.

The mixture was stirred for 1 hour 14 minutes, then water (2.88 l) was added cautiously, followed by 2 N sodium hydroxide solution (576 ml).

After stirring for 29 minutes the layers were allowed to separate overnight.

The lower aqueous alkaline layer was removed and adjusted to pH 1 by addition of concentrated hydrochloric acid.

The off-white precipitate was removed by filtration and washed with water (2 l).

After drying at 62° C. in vacuo, the title compound was obtained, m.p. 242° C.

(iii) 2-Azidocarbonyl-5-[4-(1,1-dimethylethyl)phenyl]thiophene

2-Carboxy-5-[4-(1,1-dimethylethyl)phenyl]thiophene (115.26 g) was added, with mechanical stirring, to triethylamine (44.8 g) and 4A molecular sieve dried dimethylformamide (346 ml).

The resulting solution was cooled in an ice-bath and a solution of diphenylphosphoryl azide (121.82 g) in dry dimethylformamide (58 ml) was dropped in over 15 minutes at 2.5°-15° C.

During the addition a mass of cream coloured solid separated.

After stirring for a further 5 minutes, the ice-bath was replaced by a heating mantle. The mixture was stirred for hour 40 minutes at 37±2° C., then poured into crushed ice (2 l) and water (1.5 l).

The cream coloured solid was removed by filtration then mechanically stirred in 0.1 N sodium hydroxide solution (800 ml) for 10 minutes.

The solid was filtered off and washed with water (total volume 2 l), then dried at room temperature in vacuo over silica gel, m.p. 104°.

(iv) 2-[4-(1,1-Dimethylethyl)phenyl]-5-isocyanato thiophene

A magnetically stirred solution of 2-azidocarbonyl-5-[4-(1,1-dimethylethyl)phenyl]thiophene (123.32 g) in 4A molecular sieve dried toluene (1 l) was heated under reflux for 1 hour 19 minutes.

Evaporation at 60° C. in vacuo left a dark cream coloured solid, which was dried at room temperature, m.p. 76°.

(v) 2-Cyano-N-[5-(4-(1,1-dimethylethyl)phenyl)thien-2-yl]-3-hydroxybut-2-enamide A suspension of cyanoacetone, sodium salt (40.98 g); in freshly sodium dried and distilled tetrahydrofuran (200 ml) was mechanically stirred and cooled in an ice-bath.

A slightly turbid solution of 2-[4-(1,1-dimethylethyl)phenyl]-5-isocyanatothiophene (100 g), in dry tetrahydrofuran (400 ml) was added dropwise during 40 minutes at 3°-5° C.

After stirring the mustard coloured suspension in the ice-bath for a further 20 minutes, the bath was then removed, stirring continued for 52 minutes at ambient temperature, then for 1.5 hours at 55 ±2° C. in a heating mantle.

After evaporation in vacuo the residual cream coloured paste was stirred in 0.7 N sodium hydroxide (975 ml) for 30 minutes.

Filtration removed an insoluble cream coloured solid. The alkaline filtrate was adjusted to pH 1 by the addition of concentrated hydrochloric acid, precipitating a cream coloured pasty solid which was removed by filtration, washed with water (approximately 3 l) and partially dried at 60° C. in vacuo.

This solid was stirred at reflux in absolute ethanol (2 l) for 15 minutes, then for 45 minutes in an ice-bath. After filtration, washing with ice-cold ethanol (400 ml) and drying at 60° C. in vacuo. It was further purified by stirring for 10 minutes with charcoal (5 g) in boiling ethyl acetate (2.25 l). The charcoal was removed by filtration and washed on the filter with hot ethyl acetate (300 ml). The filtrate and washings were combined and reduced in volume by 1.5 l by evaporating in vacuo.

After standing in an ice-bath for 1 hour, pale green crystals were removed by filtration, washed with 40°-60° C. petrol (100 ml) and dried at 45° C. in vacuo.

The crystalline solid was finally purified by stirring in 1N sodium hydroxide (750 ml) and ether (750 ml). The lower aqueous alkaline layer was removed and filtered to clarify. Concentrated hydrochloric acid was added to adjust to pH 1. The resulting cream coloured precipitated solid was filtered off, washed on the filter with water (2 l) and dried at 60° C. in vacuo, m.p. 226°-228° C.

The following compounds were similarly prepared.

2-Cyano-N-[5-(4-(1-cyano-1-methylethyl)phenyl)thien-2-yl]-3-hydroxybut-2-enamide, m.p. 22°-224° C. (from 2-carboxy5-[4-(1-cyano-1-methylethyl)phenyl]thiophene).

2-Cyano-N-[5-(4-fluorophenyl)thien-2-yl]-3-hydroxybut-2-enamide, m.p. 232°-234° C. (from 2-carboxy-5-(4-fluorophenyl)thiophene).

2-Cyano-N-[5-(4-chlorophenyl)thien-2-yl]-3-hydroxybut-2-enamide. m.p. 252°-254° C. (from 2-carboxy-5-(4-chlorophenyl)thiophene).

2-Cyano-N-[5-(4-(1,1-dimethylpropyl)phenyl)thien-2-yl]-3-hydroxybut-2-enamide, m.p. 211°-213° C. (from 2-carboxy-5-[(4-(1,1-dimethylpropyl)phenyl)]thiophene).

2-Cyano-N-(5-phenylthien-2-yl)-3-hydroxybut-2-enamide, m.p. 240°-241° C. (from 2-carboxy-5-phenylthiophene).

2-Cyano-N-[5-(4-methylphenyl)thien-2-yl]-3-hydroxybut-2-enamide, m.p. 245°-247° C. (from 2-carboxy-5-(4-methylphenyl)thiophene.

2-Cyano-N-[4-(4-(1,1-dimethylethyl)phenyl)thien-2-yl]-3-hydroxybut-2-enamide, m.p. 243°-246° C. (from 2-carboxy-4-[4-(1,1-dimethylethyl)phenyl]thiophene).

EXAMPLE 3

(i) Ethyl ethoxymethyleneacetoacetate

Ethyl acetoacetate (130.14 g), triethylorthoformate (148.2 g) and acetic anhydride (204.18 g) were heated under reflux for 90 minutes. The more volatile by-products were removed on a rotary evaporator, leaving a dark red oil (approx. 400 ml). This was distilled at reduced pressure through a 15 cm Vigreux column, giving 128 g of a clear oil (b.p. 100°-110° C., 1 mmHg). The product was a 1:1 mixture of Z and E ethyl ethoxymethyleneacetoacetate.

(ii) Ethyl 5-methylisoxazol-4-yl carboxylate

Hydroxylamine hydrochloride (52.6 g) was dissolved in water (150 ml) and stirred while an ice-cold solution of sodium hydroxide (30.28 g) in water (100 ml) was added. This solution was stirred for 15 minutes then absolute ethanol (600 ml) added and the solution stirred for a further 15 minutes. Ethyl ethoxymethyleneacetoacetate (128 g) was dissolved in absolute ethanol (100 ml) and added to the hydroxylamine solution. After stirring for 30 hours the solvents were removed on a rotary evaporator (bath at 45° C.). The clear oil was distilled at reduced pressure through a 15 cm Vigreux column. Product collected as a clear oil at 50°–54° C./0.5 mmHg.

(iii) 5-Methylisoxazol-4-yl carboxylic acid

Ethyl 5-methylisoxazol-4-yl carboxylate (65 g) was heated under reflux in 10 M HCl (500 ml) for 3 hours. On cooling the product crystallised out. This was filtered and dried giving 42 g of a white crystalline solid, m.p. 134°–136° C.

(iv) 5-Methylisoxazol-4-yl carbonyl chloride

Thionyl chloride (118 g) was added to 5-methylisoxazol-4-yl carboxylic acid (42 g) and stirred at room temperature as dimethylformamide (0.2 ml) was added. The solution was heated under reflux for 2 hours with stirring. Excess thionyl chloride was removed in vacuo at 50° C., then the residue was distilled through a 15 cm Vigreux column at reduced pressure to give an oil, b.p. 32°–34° C./0.1 mmHg.

(v) 2-Amino-4-[4-(1,1-dimethylethyl)phenyl]thiazole

This compound had m.p. 145.5° C. and was prepared in accordance with the method used by Eilingsfeld, H., Neumann, P.; Seybold, G., Lenke D. and Friedrich, L., European Patent Application No. 44,442.

(vi) N-[4-(4-(1,1-Dimethylethyl)phenyl)thiazol-2-yl]-5-methylisoxazol-4-yl carboxamide A mixture of 2-amino-4-[4-(1,1-dimethylethyl)phenyl]-thiazole (8 g) and 3A molecular sieve dried pyridine (2.72 g) in 3A mole sieve dried dichloromethane (20 ml) was magnetically stirred, with ice-bath cooling. The reaction was carried out in oven dried apparatus under nitrogen.

A solution of 5-methylisoxazol-4-yl carbonyl chloride (5 g) in dry dichloromethane (50 ml) was added dropwise, during 32 minutes at 3.5°–9° C.

The ice-bath was removed and stirring continued for a further 21.25 hours at ambient temperature.

The reaction mixture was washed with 0.5 N hydrochloric acid (2×20 ml), then water (2×20 ml). After drying over MgSO$_4$, filtering and evaporating at 55° C. in vacuo a residual cream coloured solid was obtained, m.p. 210° C.

The combined acid and water washings deposited a white solid which was filtered off and washed with water (2×100 ml). After drying at 60° C. in vacuo the title compound had a m.p. 219°–220° (decomposition).

(vii) 2-Cyano-N-[4-(4-(1,1-dimethylethyl)phenyl)thiazol-2-yl]-3-hydroxybut-2-enamide N-[4-(4-(1,1-Dimethylethyl)phenyl)thiazol-2-yl]-5-methylisoxazol-4-yl carboxamide (6.02 g) was added to a solution of sodium hydroxide (0.496 g) in water (20 ml), dimethylsulphoxide (10 ml) and absolute ethanol (150 ml).

After stirring at ambient temperature for 22 hours, more sodium hydroxide (0.496 g) in water (10 ml) was added. Stirring was continued for a further 24 hours, then the clear solution was evaporated at 54° C. in vacuo to leave a mustard coloured oil.

The oil was shaken with 0.04 N sodium hydroxide solution (2.5 l) and ether (200 ml).

Filtration removed an insoluble solid, which was washed with ether (200 ml) before suspending in 2 N hydrochloric acid (75 ml) and keeping in an ultrasonic bath for 5 minutes.

After filtering and washing with water (6×50 ml) the cream coloured solid was dried at 60° C. in vacuo. Recrystallisation from boiling ethyl acetate (300 ml) yielded the pure butenamide and after drying at 60° C. in vacuo the product had a m.p. 226°–228° C. (decomposition).

The following compound was similarly prepared 2-Cyano-N-(5-phenylthiazol-2-yl)-3-hydroxybut-2-enamide, m.p. >260° C.

EXAMPLE 4

(i) 4-(1,1-Dimethylethyl)phenylmethyl ketone 4-(1,1-Dimethylethyl)benzene (50 g) and acetyl chloride (32.2 g) were added together dropwise to a mechanically stirred suspension of aluminium chloride (52.2 g) in dichloromethane (100 ml dry) under nitrogen over one hour at room temperature when the mixture became a dark red/brown. It was stirred at room temperature for a further 3½ hours, poured on to ice (800 ml +400 ml) and concentrated HCl added (~100 ml), allowed to stand while the ice melted and extracted with diethyl ether (5×200 ml). It was then dried over MgSO$_4$ and the solvent removed in vacuo to give a red oil which was purified by vacuum distillation, b.p. 70° C./0.25 mmHg).

(ii) 1-(N,N-Dimethylamino)-3-(4-(1,1-dimethylethyl)phenyl)prop-1-en-3-one

To 4-(1,1-Dimethylethyl)phenylmethyl ketone (5 g) in absolute ethanol (50 ml) heated to 80° C. with stirring was added N,N-dimethylformamide diethyl acetal (5.01 g) in absolute ethanol (2.5 ml) dropwise over 5 minutes, heated under reflux with stirring overnight and the reaction followed by tlc. The excess ethanol was removed under reduced pressure to give a brown oil which was cooled in cardice to give a yellow solid. The product was recrystallised from petroleum ether 40°–60° C.

(iii) 2-Amino 4-(4-(1,1-dimethylethyl)phenyl)pyrimidine

Sodium metal (10.4 g) was added to absolute ethanol (40 ml). When all the sodium had dissolved, the sodium ethoxide solution so formed was added to a mixture of guanidine carbonate (1.56 g) and (1-(N,N-dimethylamino)-3-(4-(1,1-dimethylethyl) phenyl)prop-1-en-3-one (2.5 g) dissolved in absolute ethanol (40 ml) and the mixture heated under reflux with stirring overnight. The reaction was followed by tlc. On cooling the solid material formed was filtered and washed with water to remove Na$_2$CO$_3$ to give a white crystalline solid, m.p. 186° C.

(iv) 2-Cyano-N-[4-(4-(1,1-dimethylethyl)phenyl)pyrimid-2-yl]-3-hydroxybut-2-enamide The above compound was prepared from the intermediate of stage (iii) by the methods described in Example 3. The product had a melting point 224°–225° C.

EXAMPLE 5

(i) 2-(4-(1,1-Dimethylethyl)phenyl-1-methylpyrrole

Butyl lithium (1.55M in hexane, 79.65 ml) was added dropwise with stirring at −70° C. to 1-methylpyrrole (10 g) in dry tetrahydrofuran (80 ml) under nitrogen during 15 minutes, then warmed to room temperature (20° C.) for 1 hour before adding this solution to anhydrous zinc chloride (18.5 g) in dry tetrahydrofuran (160 ml). (The zinc chloride was dried in an oven at 300° C. for 16 hours prior to use.) The resulting mixture was stirred at room temperature for 1 hour before being added dropwise with stirring to 1-bromo-4-(1,1-dimethylethyl)-benzene (17.52 g) in dry tetrahydrofuran (200 ml) containing bis(triphenylphosphine)palladis II chloride (1.18 g). The resulting mixture was stirred over night at room temperature, then heated under reflux during 2 hours, cooled to room temperature, allowed to stand for 16 hours at room temperature before pouring into ethyl acetate (1000 ml), washing with water (2×100 ml), 2 M hydrochloric acid (2×100 ml) and saturated sodium hydrogen carbonate solution (3×250 ml). The ethyl acetate solution was dried (MgSO$_4$) and the solvent removed in vacuo to give crude product which was distilled at 135° C./0.1 mm Hg.

(ii) 5-(4-(1,1-Dimethylethyl)phenyl-1-methylpyrrole-2-carboxylic acid

Butyl lithium (1.55 M in hexane, 24.84 ml) was added dropwise with stirring to 2-(4-(1,1-dimethylethyl)phenyl-1-methylpyrrole (8 g) in dry tetrahydrofuran (150 ml) during 1 hour at −75° C. under nitrogen. After warming to room temperature and stirring for 1 hour the mixture was poured into diethyl ether (400 ml) containing crushed carbon dioxide solid (600 g) and the carbon dioxide allowed to evaporate. The ethereal solution was extracted with 2 M sodium hydroxide (3×100 ml) acidified with 5 M hydrochloric acid, and the aqueous solution extracted with diethyl ether (2×100 ml) ethyl acetate (2×100 ml). The extracts were dried (MgSO$_4$) and the
solvent removed in vacuo to give 5-(4-(1,1-dimethylethyl)-phenyl-1-methylpyrrole-2-carboxylic acid, m.p. 192°–194° C.

(iii) 2-Cyano-N-[5-(4-(1,1-dimethylethyl)phenyl)-1-methyl pyrrol-2-yl]-3-hydroxybut-2-enamide The above compound was prepared by the methods described in Example 2, employing the intermediate described above.

EXAMPLE 6

(i) Methyl 5-bromofuran-2-carboxylate

Boron trifluoride methanol (6.3 ml, 7.6 g) was added to a stirred solution of 5-bromofuran-2-carboxylic acid (10 g) in methanol (90 ml) and heated under reflux under nitrogen for 5 hours. More boron trifluoride methanol (5 ml) was added and the mixture heated under reflux for 5 hours, allowed to cool to room temperature and stand for 10 hours before the solvent was removed in vacuo and the residue poured into saturated sodium hydrogen carbonate solution (300 ml) and extracted with ethyl acetate (3×200 ml). The extract was washed with saturated sodium hydrogen carbonate solution (2×100 ml), dried over MgSO$_4$, and the solvent removed in vacuo to give methyl 5-bromofuran-2-carboxylate, m.p. 62° C.

(ii) 1-(1,1-Dimethylethyl)-4-tributylstannylbenzene

1-Bromo-4-(1,1-dimethylethyl)benzene (10.656 g) in dry tetrahydrofuran (40 ml) was added dropwise with stirring to magnesium metal (1.264 g) in dry tetrahydrofuran (10 ml). After the reaction had been initiated by warming the 1-bromo-4-(1,1-dimethylethyl)benzene was added dropwise at such a rate to maintain boiling of the solvent. After the addition the mixture was heated under reflux for 1 hour then cooled to room temperature and tri-n-butyltin chloride (14.12 ml) in dry tetrahydrofuran (20 ml) was added dropwise. The mixture was heated under reflux for 1 hour poured into ice water (300 ml), extracted with diethyl ether (2×100 ml), washed with sodium hydrogen carbonate (50 ml), dried (MgSO$_4$) and the solvent removed in vacuo to give a yellow liquid which was poured on to flash silica gel (25 g) on a sinter. The product was washed through with hexane and the hexane was removed in vacuo to give a colourless liquid which was used directly in the next reaction.

(iii) Methyl 5-(4-(1,1-dimethylethyl)phenylfuran-2-carboxy late

Methyl 5-bromofuran-2-carboxylate (2 g), 4-(1,1-dimethylethyl) 4-(tributylstannyl)benzene and bis-(triphenylphosphine)palladium II chloride (0.377 g) in dry tetrahydrofuran (25 ml) were heated under reflux under nitrogen for 8 hours, cooled, poured into ethyl acetate (100 ml), washed with sodium hydrogen carbonate (3×100 ml) and dried (MgSO$_4$). The solvent was removed in vacuo to give methyl 5-(4-(1,1-dimethylethyl)phenylfuran-2-carboxylate,

(iv) 5-(4-(1,1-Dimethylethyl)phenylfuran-2-carboxylic acid

Sodium hydroxide (1.42 g) in water (17.75 ml) was added to a vigorously stirred solution of methyl 5-(4-(1,1-dimethylethyl)phenylfuran-2-carboxylate (4.579 g) in tetrahydrofuran (100 ml) and stirred at room temperature for 17 hours, the solvent was removed in vacuo and the residue dissolved in 10% sodium hydrogen carbonate solution (200 ml) then acidified with 2 M hydrochloric acid. The mixture was extracted with diethyl ether (3 x 200 ml), the ether washed with water and dried (MgSO$_4$) The solvent was removed in vacuo to give 5-(4-(1,1-dimethylethyl)phenylfuran-2-carboxylic acid, m.p. 230° C.

(v) 2-Cyano-N-[5-(4-(1,1-dimethylethyl)phenyl)-1-furan-2-yl]-3-hydroxybut-2-enamide The above compound was prepared by the methods described in Example 2, employing the intermediate described above.

EXAMPLE 7

The following pharmaceutical formulations are given by way of example:

(i) Injection formulation

An injection formulation containing 5 mg/ml of active ingredient is prepared from the following

| Active ingredient | 250 mg |
| --- | --- |
| 0.1 M Sodium hydroxide | 10 ml |
| N/10 Hydrochloric acid | 2 ml |
| 5% Poloxamer F68 in isotonic saline to | 50 ml |

(ii) Hard gelatin capsule formulation

| Active ingredient | 100 mg |
| --- | --- |
| 1% Silicone starch | 50 mg |
| Starch flowable | 50 mg |

(iii) Tablet formulations

| Active ingredient | 100 mg |
| --- | --- |
| Microcrystalline cellulose | 185 mg |
| Carboxymethyl cellulose sodium (crosslinked) | 3 mg |
| Povidone | 10 mg |
| Magnesium stearate | 1 mg |

EXAMPLE 8

The concanavalin A response of rat spleen cells was used as a primary in vitro assay to determine the activity of the compounds of the invention. Many methods for the determination of concanavalin A response are described in the literature. The method employed was similar to that described by Lacombe P. et al, FEBS 3048 191, 227–230. This method was altered insofar as Hepes was excluded, $2 \times 10^5$ cells were used per culture well, and concanavalin A employed at 3 μg/ml. 2-Mercaptoethanol was a requirement ($2 \times 10M^{-5}$) and 0.1 μCi of tritiated thymidine was added 4 hours before cell harvesting.

For instance compounds of the invention described in Example 2 all exhibited a greater than 50% inhibition at a dosage level of 10 micromolar.

We claim:

1. A compound of the formula

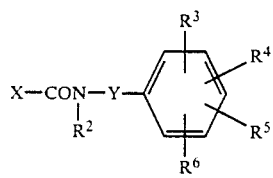

in which X is $R^1(HO)C{=}C(CN)—$ or $R^1(CO)—CH(CN)—$, $R^1$ and $R^2$ are each hydrogen or $C_{1-6}$ alkyl, $R^3$, $R^4$, $R^5$ and $R^6$ are each hydrogen, hydroxy, halogen, nitro, cyano, carboxy, $C_{1-4}$ alkyl, $C_{1-4}$ alkoxy, $C_{1-4}$ alkylthio, halo-substituted $C_{1-4}$ alkyl, halo-substituted $C_{1-4}$ alkoxy, halo-substituted $C_{1-4}$ alkylthio, $C_{2-5}$ alkoxycarbonyl, optionally substituted phenyl, optionally substituted phenoxy, $R'R''N—$ where $R'$ and $R''$ are each hydrogen or $C_{1-4}$ alkyl or $R'R''CONH—$ where $R'$ and $R''$ is $C_{1-4}$ alkyl, or a group of the formula $—CR^7R^8R^9$ in which $R^7$, $R^8$ and $R^9$ are each $C_{1-6}$ alkyl, halo-substituted $C_{1-6}$ alkyl or optionally substituted phenyl, or $R^7$ and $R^8$, together with the carbon atom to which they are attached, form a bicycloalkyl group containing 4 to 9 carbon atoms, and Y is a thiophene, furan, pyrrole, or thiazole ring optionally substituted with one or two $C_1$–$C_4$ alkyl groups; and salts thereof.

2. A compound according to claim 1 in which $R^3$, $R^4$ and $R^5$ are hydrogen, and X is

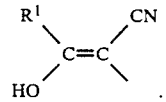

3. A compound according to claim 2 in which $R^1$ is methyl and Y is thiophene.

4. A compound according to claim 1 in which $R^3$, $R^4$, and $R^5$ are hydrogen and $R^6$ is hydrogen, $C_{1-4}$ alkyl, halo-substituted $C_{1-4}$ alkyl or $—CR^7R^8R^9$ in which $R^7$, $R^8$ and $R^9$ are each $C_{1-4}$ alkyl.

5. A compound according to claim 1 of the formula

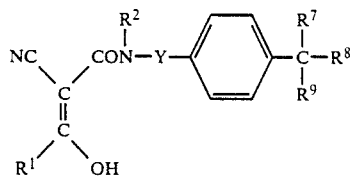

in which $R^1$ is $C_{1-4}$ alkyl, $R^2$ is hydrogen or methyl, and $R^6$, $R^7$ and $R^8$ are each $C_{1-4}$ alkyl; and salts thereof.

6. 2-Cyano-N-[5-(4-(1,1-dimethylethyl)phenyl)thien-2-yl]-3-hydroxybut-2-enamide.

7. A pharmaceutical formulation comprising a compound according to claim 1 or a pharmaceutically-acceptable salt thereof in association with a pharmaceutically-acceptable carrier or diluent thereof.

8. A method of treating a mammal, including a human, suffering or susceptible to inflammation or a disease in which leukotrienes are implicated, which comprises administering an effective amount of a compound of formula (I) as defined in claim 1, or a pharmaceutically-acceptable salt thereof.

* * * * *

UNITED STATES PATENT AND TRADEMARK OFFICE
CERTIFICATE OF CORRECTION

PATENT NO. : 4,983,619

DATED : January 8, 1991

INVENTOR(S) : Peter T. Gallagher and Terence A. Hicks

It is certified that error appears in the above-identified patent and that said Letters Patent is hereby corrected as shown below:

Claim 1, column 20, line 10 change "or R'R" CONH- where R' and R" is" to -- or R''' CONH- where R''' is ---.

Signed and Sealed this

Seventh Day of July, 1992

Attest:

DOUGLAS B. COMER

Attesting Officer
Acting Commissioner of Patents and Trademarks